US011154242B2

(12) United States Patent
Mathew et al.

(10) Patent No.: US 11,154,242 B2
(45) Date of Patent: Oct. 26, 2021

(54) METAL-ION ELECTROCHEMICAL BIOSENSOR AND USE THEREOF

(71) Applicants: RUSH UNIVERSITY MEDICAL CENTER, Chicago, IL (US); THE BOARD OF REGENTS OF THE UNIVERSITY OF TEXAS SYSTEM, Austin, TX (US)

(72) Inventors: Mathew T. Mathew, Elmhurst, IL (US); Shalini Prasad, Richardson, TX (US); Markus A. Wimmer, Chicago, IL (US); Nadim J. Hallab, Oak Park, IL (US); Joshua Jacobs, Wilmette, IL (US)

(73) Assignees: Rush University Medical Center, Chicago, IL (US); Board of Regents, The University of Texas System, Austin, TX (US)

(*) Notice: Subject to any disclaimer, the term of this patent is extended or adjusted under 35 U.S.C. 154(b) by 403 days.

(21) Appl. No.: 15/124,893

(22) PCT Filed: Mar. 11, 2015

(86) PCT No.: PCT/US2015/019899
§ 371 (c)(1),
(2) Date: Sep. 9, 2016

(87) PCT Pub. No.: WO2015/138571
PCT Pub. Date: Sep. 17, 2015

(65) Prior Publication Data
US 2017/0014072 A1 Jan. 19, 2017

Related U.S. Application Data

(60) Provisional application No. 61/951,354, filed on Mar. 11, 2014.

(51) Int. Cl.
*A61B 5/00* (2006.01)
*G01N 17/00* (2006.01)
(Continued)

(52) U.S. Cl.
CPC ............ *A61B 5/4851* (2013.01); *A61B 5/145* (2013.01); *G01N 17/006* (2013.01); *G01N 27/3273* (2013.01); *A61F 2/32* (2013.01)

(58) Field of Classification Search
CPC .............. G01N 27/3273; G01N 17/006; A61B 5/145; A61B 5/4851; A61F 2/32
See application file for complete search history.

(56) References Cited

U.S. PATENT DOCUMENTS

| | | | |
|---|---|---|---|
| 4,877,492 A | 10/1989 | Uematsu et al. |
| 4,995,959 A | 2/1991 | Metzner |
| 5,288,374 A | 2/1994 | Watanabe et al. |
| 5,978,692 A | 2/1999 | Vukan et al. |

(Continued)

FOREIGN PATENT DOCUMENTS

| WO | WO2013/021357 | 2/2013 |
| WO | WO2014/145491 | 9/2014 |

OTHER PUBLICATIONS

Jacobs, Joshua J., et al.; Metal Release in Patients Who Have Had a Primary Total Hip Arthroplasty; The Journal of Bone and Joint Surgery, Inc., vol. 80-A, No. 10, Oct. 1998 (Year: 1998).*

(Continued)

*Primary Examiner* — Edward J. Schmiedel
(74) *Attorney, Agent, or Firm* — Barnes & Thornburg LLP (57) ABSTRACT

One aspect of the invention provides a method of determining metal ion levels in the patents due to corrosion and wear processes of the metallic implant in a human or veterinary patient. One embodiment provides a cost effective and patient driven early diagnostic method which has a potential (Continued)

application in orthopedics and dentistry. In one embodiment, the method includes the use of an electrochemical biosensor to detect metal ions or particles in a sample taken from a patient having a metallic implant.

13 Claims, 6 Drawing Sheets

(51) Int. Cl.
*A61B 5/145* (2006.01)
*G01N 27/327* (2006.01)
*A61F 2/32* (2006.01)

(56) References Cited

U.S. PATENT DOCUMENTS

2003/0094383 A1* 5/2003 Kermani ............ G01N 27/3273 205/777.5
2008/0246243 A1 10/2008 Matsuoka
2016/0015320 A1* 1/2016 Gilbert ................ A61B 5/4851 600/547

OTHER PUBLICATIONS

International Search Report for PCT/US2015/019899 dated May 11, 2015, 2 pgs.
Written Opinion for PCT/US2015/019899 dated May 11, 2015, 5 pgs.
International Preliminary Report on Patentability for PCT/US2015/019899 dated Sep. 22, 2016, 7 pgs.
Vinay J. Nagaraj, et al., "NanoMonitor: a miniature electronic biosensor for glycan biomarker detection", Nanomedicine (2010) 5(3), 369-378.
Pichetsurnthorn, P. et al., "Nanoporous impedemetric biosensor for detection of trace atrazine from water samples", Biosensors and Bioelectronics 32 (2012) 155-162.
Mathew, M.T. et al., "Construction of a tribocorrosion test apparatus for the hip joint: Validation, test methodology and analysis", Wear 271 (2011) 2651-2659.

* cited by examiner

Fig 1. Metal ion distribution-Tribocorrosion test-HC-CoCrMo-Potentiostatic conditions

METAL-ION ELECTROCHEMICAL BIOSENSOR AND USE THEREOF

RELATED APPLICATIONS

This application is a National Stage of PCT/US2015/019899, filed Mar. 11, 2015, which claims the benefit of the filing date of U.S. Provisional Patent Application No. 61/951,354, filed Mar. 11, 2014, the contents of which applications are hereby incorporated by reference.

TECHNICAL FIELD

The present invention generally relates to electrochemical biosensor technology and the use of such technology for the detection of metal ions and metal nanoparticles in a sample taken from a patient having a metallic implant.

BACKGROUND

Hip replacements remain one of the leading procedures regarding success rates and research advancements in Orthopedics today. However, biocompatibility and implant longevity are still severely limited by corrosion and wear (tribology) or combined action of both of them known as "tribocorrosion" which are considered as main failure mechanisms of the implants. With corrosive and tribocorrosive processes acting upon the metal implants in the body, there is a net release of metal ions or particles (particles further disintegrated into metal ions) into the synovial joint environment diffusing into systemic vasculature and organ systems. The release of these metal ions/nanoparticles can result in painful inflammation, cell damage, infection, revision surgeries, implant loosening, and malignancies. Metal ion levels, caused from implant placement, are generally seen to increase within 3 to 24 months of the hip replacement, for instance, these levels can rise up to 556 mg/L from 13 mg/L of Cobalt particle from CoCrMo implants.

Although the effects of metal ions/particles have been studied on different body systems, their effect on the corrosion kinetics of the metal implant are not well understood and have not been thoroughly investigated. Additionally, methods for testing metal ion levels in synovial fluid and blood are very expensive with current laboratory techniques. In orthopedics and dentistry, there is no patient driven diagnostic system and cost effective clinical method is available to detect metal ion levels

SUMMARY OF THE PREFERRED EMBODIMENTS

In one aspect, the present invention provides a method for determining increasing metal ion level due to the corrosion process occurring in a metallic implant present in a human or veterinary patient. In one embodiment, the method includes adding a sample taken from the patient to an electrochemical cell and measuring impedance at an electrode of the electrochemical cell to obtain a sample impedance value. The sample impedance value is a measure of the presence of metal ions from the metallic implant in the sample and is indicative of the extent of corrosion of the metallic implant. In one embodiment, the impedance is measured using a potentiostat.

Samples taken of the patient can be: a blood sample, a urine sample or a synovial fluid sample. In some embodiments, the implant can be a metal-on-metal implant or metal based hip implant. For example, the metallic implant may be a dental implant, a spinal implant, a hip joint, a knee joint, an ankle joint or a shoulder joint. In one embodiment, the metal ions measured may be cobalt, chromium, molybdenum (from COCrMo alloy), titanium, vanadium, aluminum (from Ti6Al4V alloy) or combination of these elements.

The electrochemical cell may be a metal-ion electrochemical biosensor including at least two electrodes in fluid contact with a sample chamber. In one embodiment, the electrochemical cell includes a working electrode, a counter electrode and a reference electrode in fluid contact with the sample chamber. The electrodes may be gold or platinum electrodes.

The impedance (Z) value obtained for the sample may be compared to an impedance value obtained from a reference sample containing a known amount of metal ions. In certain embodiments, the sample is obtained from the patient at between 2 and 36 months after implantation of the metallic implant. In other embodiments, a time series of samples taken from the patient sample impedance values measured for each sample to obtain a measure of metal ions, which may indicate corrosion or tribocorrosion process of the metal implant in in-vivo conditions.

DETAILED DESCRIPTION OF THE PREFERRED EMBODIMENTS

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

For the purpose of promoting an understanding of the principles of the invention, reference will now be made to embodiments, some of which are illustrated in the drawings, and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. In the discussions that follow, a number of potential features or selections of assay methods, methods of analysis, or other aspects, are disclosed. It is to be understood that each such disclosed feature or features can be combined with the generalized features discussed, to form a disclosed embodiment of the present invention.

One aspect of the present invention provides a method for monitoring the integrity of a metal implant to determine the presence of implant corrosion, indicated by a loss of metal ions/particles from the implant; therefore, resulting in a net increase of metal ions concentration in the synovial fluid, blood, or urine. The early detection of metal ions will assist in avoiding possible side effects on the patients and clinicians can formulate early clinical management before a catastrophic failure of the implant. For example, the implant may be monitored by determining the presence of metal, from decay of the implant, in the body tissue of the patient. In various embodiments, the presence of such metal ions or particles in a sample taken from a human or veterinary patient having such an implant is determined. The implant may be a metal-on-metal implant in which two contacting metallic surfaces move in respect to one other or any implant with a metal component to it. For example, the implant may be a dental implant, a spinal implant, a hip joint, a knee joint, an ankle joint or a shoulder joint. The metal present in the implant, and detected by the disclosed detection methods, may be, for example, cobalt, chromium, molybdenum titanium or a combination or alloy of at least two of these metals.

In one embodiment, the method includes the measurement of metal from the implant that is present in a sample taken from the patient. Some sample types include: a blood sample, a urine sample or a synovial fluid sample. The presence of metal particles may be determined by an electrochemical measurement method. In certain embodiments, a sample from the patient is placed in fluid contact with the electrodes of an electrochemical cell and the impedance measured at an electrode of the cell. The impedance may be measured using, for example, a potentiostat. In general, increasing metal content in the sample has been found to reduce the impedance value, by increasing the conductivity of the solution. The method therefore allows for a determination of the amount of metal ions in the sample in accordance with the measured impedance or percentage change in the impedance values.

In certain embodiments, the impedance value obtained for the sample is compared to an impedance value obtained from one or more reference sample(s) containing a known amount of metal ions or particles. For example, the sample impedance value may be compared with impedance values obtained from a sample known to be free of metal corrosion products (fresh solution) from the type of implant present in the patient's body. In other embodiments, the sample impedance value may be compared with a series of reference values obtained from samples containing differing amounts of the corrosion products from such an implant.

Samples may be obtained from the patient both before the implant is introduced into the patient and/or at one or more time points after implantation. In certain embodiments, the sample is obtained from the patient at between 2 and 36 months, or between 2 and 24 months after implantation of the metallic implant. In some embodiments, a series of samples are taken from the patient at a series of time points after implantation and measured using the MIEB to obtain a series of sample impedance values. This process allows the time course of any corrosion to be monitored at compared to a base control value.

Metal-ion Electrochemical Biosensor

One aspect of the present disclosure provides a method of determining metal ions levels using a metal-ion electrochemical biosensor (MIEB). Previously, the measurement of such metal levels in body fluids had required the use of complex instrumental, such as graphite furnace atomic absorption spectrophotometry (GFASS). In one embodiment, the MIEB provides a cost-effective screening test effective in gauging the extent of any corrosion of a metal implant, thereby assisting physicians, and orthopedic patients with implant clinical management. In one embodiment, the MIEB is a patient driven early diagnostic system, by which patient will be aware of the metal ion level in his/her body due to the implant. Together with his/her physicians and by regulating the daily activities, the sudden peak of such metal ion levels and subsequent serious side effects on the patient can be avoided.

The biosensor platform is based on a nanoporous impedemetric biosensor device (Pichetsurnthorn, P. et al., "Nanoporous impedemetric biosensor for detection of trace atrazine from water samples" Biosensors and Bioelectronics 32 (2012) 155-162; Nagaraj, V. J. et al, "NanoMonitor: a miniature electronic biosensor for glycan biomarker detection" Nanomedicine (2010) 5(3), pp. 369-378). One embodiment of the biosensor includes a base platform having at least a working electrode and a counter electrode present on one surface. In certain embodiments, the device also includes a reference electrode. A housing is positioned over the electrodes and provides a sample chamber in fluid contact with the electrodes. The housing includes a sample entry port allowing addition of a liquid sample to the sample chamber. The sample contacts with the electrodes forming an electrochemical cell allowing for the determination of the metal ion/particle amount in the sample by a voltammetric technique. For example, a potentiostat may be connected to the electrodes of the MIEB and the resulting impedance is measured.

The construction of one example of a MIEB will now be described in more detail with reference to a two electrode device having a printed circuit board (PCB) as the base platform. The PCB may have dimensions of, for example, 19 mm×30 mm. The dimensions of the electrodes and the electrode design may be such as to ensure maximum surface contact between the electrodes and the sample. In one embodiment, the electrodes are in the form of concentric branched gold circular patterns. For example, the outer diameter of the gold electrodes may be 13 mm and the diameters of the inner branches 10 mm and 5 mm. The gold electrodes have two electrical leads connected to electrical outlet contacts, one connecting the working electrode (WE) and the second connecting the counter electrode (CE). For example, the gold electrodes may be manufactured by depositing gold of thickness of 2-5 micro-inches over 125 micro-inches of nickel. The gold may be plated on top of copper which was 1.4 milli-inches thick. The outer metal patterns can be passivated with a polymer layer.

The printed circuit board chip may be connected to the impedance measuring unit, for example a potentiostat, through soldered contacts to the WE and CE. In order to achieve fluid confinement on the biosensor platform, a housing unit may be bonded to the PCB using a suitable adhesion agent (for example, 3M adhesive tape—300 LSE) to form a sample chamber in fluid-contact with the electrodes. The housing unit may include a sample entry port allowing the addition of a liquid sample to the cell.

Example 1

Tribocorrosion Tests

A series of tribocorrosion experiments are conducted for different lengths of time simulating wear and corrosion exposure of the implant from walking of a person up to 100,000 steps (cycles) with a hip implant (1 Hz frequency.) The test protocol is as described in Mathew, M. T. et al. Wear 271 (2011) 2651-2659 using bovine calf serum (BCS, 30 g/L protein concentration) as the test fluid. Eight representative samples are taken at seven increasing sliding cycles (3.1K, 6.3K, 12.5K, 25K, 50K, 75K, and 100K).

Example 2

Inductively Coupled Plasma Mass Spectrometry Analysis

Figure 1:
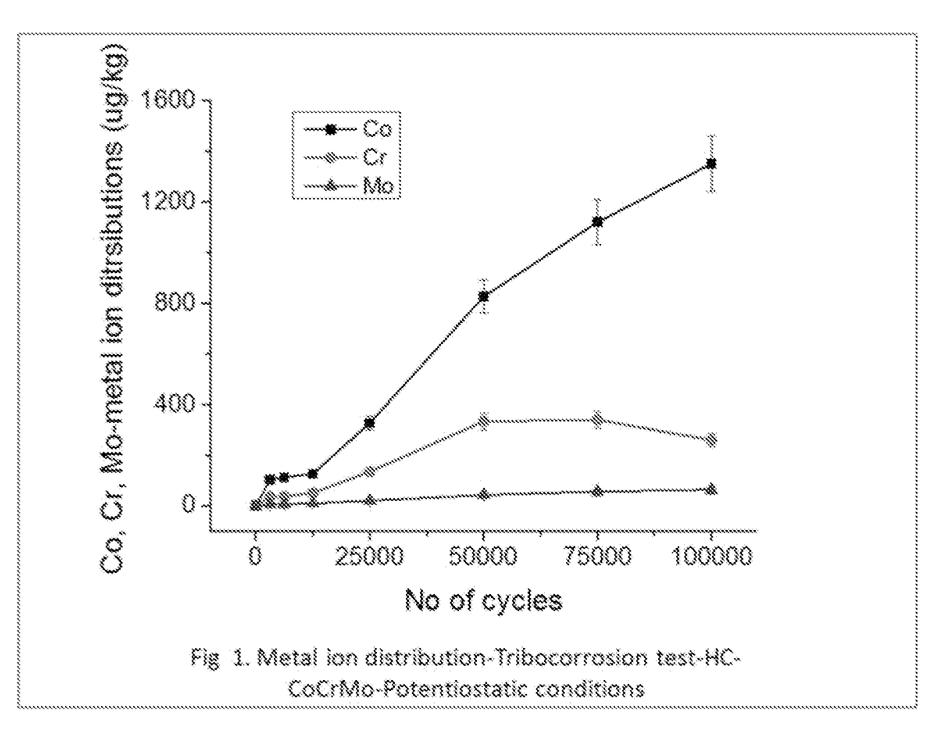
FIG. 1 is a graph showing the change in metal particle concentration for samples taken at various stages of a tribocorrosion test. The metal amounts were measured by Inductively Coupled Plasma Mass Spectrometry (ICPMS).

Metal particle distributions (Co, Cr and Mo) in the eight samples obtained in experiment 1 are analyzed by Inductively Coupled Plasma Mass Spectrometry (ICPMS). The particle distributions are as shown in in FIG. 1. Metal concentration is shown to generally increase with increasing sliding durations.

Biosensor Analysis

Figure 2:
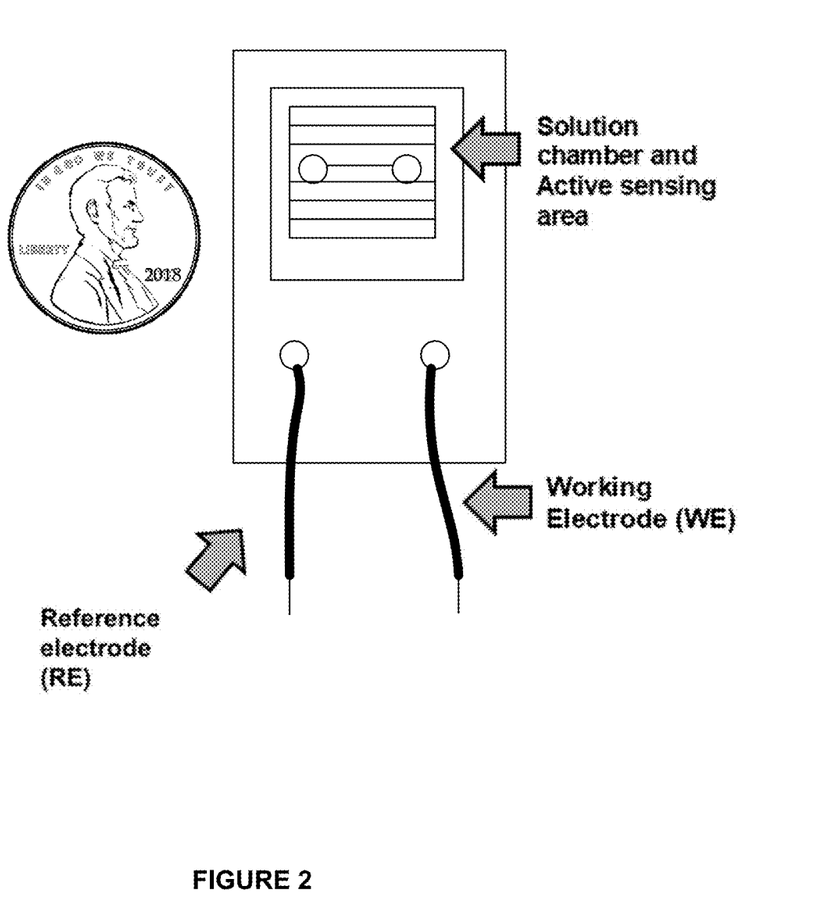
FIG. 2 is an illustration of a metal-ion electrochemical biosensor (MIEB).

The biosensor chip is a three-electrode system with the working principle based on electrochemistry. The biosensor uses 100-200 micro-liters of sample volume per analysis. A picture of an exemplifier biosensor printed circuit board design of chip is provided in FIG. 2. The assembled device has a polymer manifold to contain fluid on the gold sensing site. Impedance is measured using a potentiostat (Gamry Instruments, USA).

Figure 3:
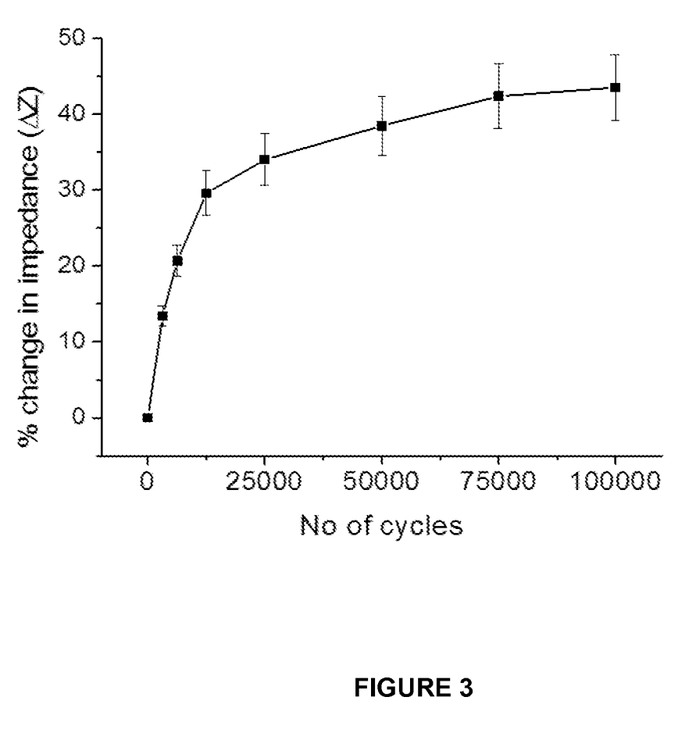
FIG. 3 is a graph showing percentage change in impedance as measured by a MIEB.

The metal particle distributions are measured by the biosensor as a function of sliding cycles are presented in Table 1 and graphically in FIG. 3. Generally, as metal content increases, a decrease in impedance values is seen. By keeping the control BCS as baseline, change in impedance is estimated ($\Delta Z$) and the percentage change in impedance is also determined (%$\Delta Z$) as listed in FIG. 3. Interestingly, there is sudden increase in impedance in the initial range of cycles and then a slower increment after about 12,500 cycles. The % $\Delta Z$ obtained by using the biosensor for 100K cycles is 43.5%, which compares well with the data received by corrosion testing using a potentiostat (%$\Delta Z$: 36.03, see below).

TABLE 1

Testing: Metal distributions as a cycles

| Sample | Mean Z (ohms) | $\Delta Z$ (ohms) | % Change | |
|---|---|---|---|---|
| Control BCS | 3943.32 | 0.00 | 0.00 | Biosensor particle |
| 3125 | 3573.37 | 369.95 | 9.38 | function of sliding |
| 6250 | 3377.83 | 565.49 | 14.34 | |
| 12500 | 2864.73 | 1078.59 | 27.35 | |
| 25000 | 2801.31 | 1142.01 | 28.96 | |
| 50000 | 2547.54 | 1395.77 | 35.40 | |
| 75000 | 2420.06 | 1523.26 | 38.63 | |
| 100000 | 2386.69 | 1556.63 | 39.48 | |

Corrosion Testing

Basic electrochemical tests are conducted on CoCrMo alloy samples with two solutions: BCS solution with high metal content (last point-100K cycles referred to as "Used BCS") to simulate synovial fluid after wear and pure BCS as a control ("Control BCS"). The CoCrMo samples are high carbon disks 12 mm in diameter with a surface roughness below a Ra value of 20 nm. The total exposed disk surface area to the solution is 0.38 cm$^2$. In each experiment (N=3), the following sequence of tests are conducted: open circuit potential (OCP), potentiostat (PS), OCP, electrochemical impedance spectroscopy (EIS), cyclic polarization, and OCP with potential at $E_{corr}$. A Warburg circuit model is used in calculating impedance parameters. The Corrosion Potential ($E_{corr}$), Corrosion rate ($I_{corr}$), and total Impedance (Z) are estimated by developing a equivalent electrical circuit.

Figure 4:
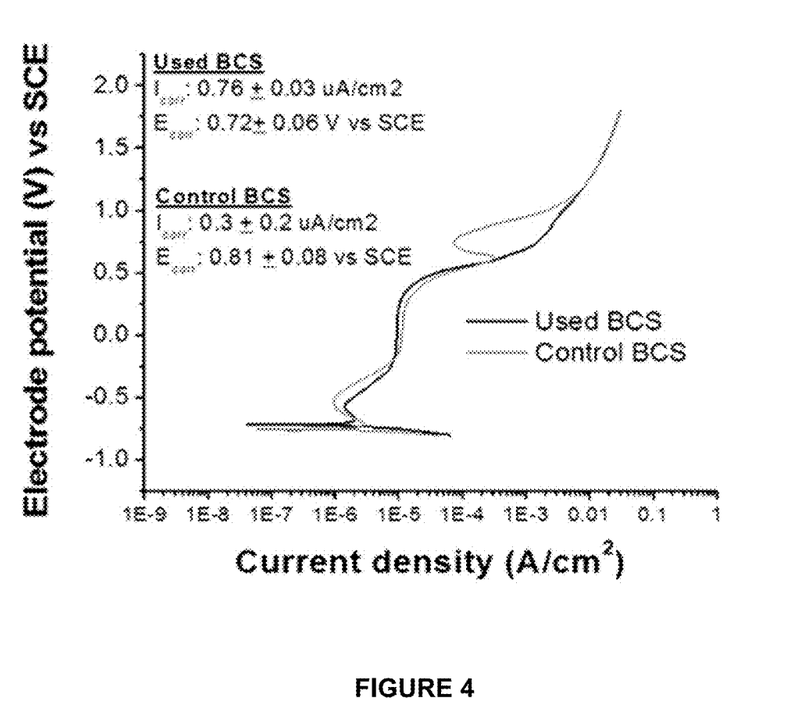
FIG. 4 is a graph showing potentiodynamic curves for used spiked (metal ions and particles) bovine calf serum (BCS) and control BCS (unspiked sample) from an electrochemical test.
Figure 5:
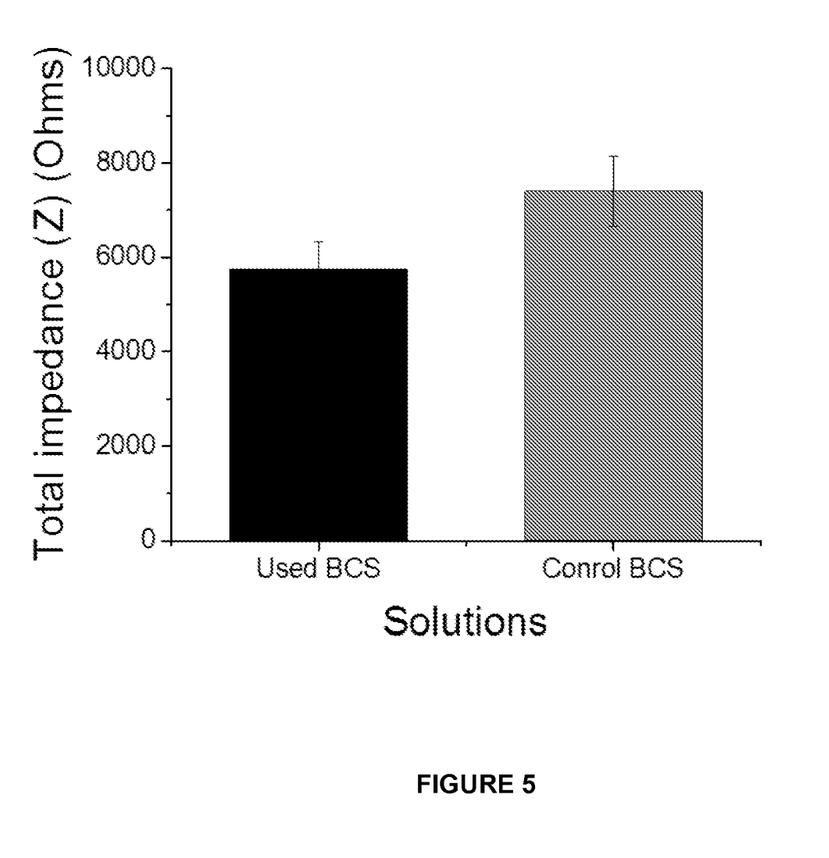
FIG. 5 is a bar graph showing total impedance obtained from both spiked and control BCS tests using a MIEB.
Figure 6:
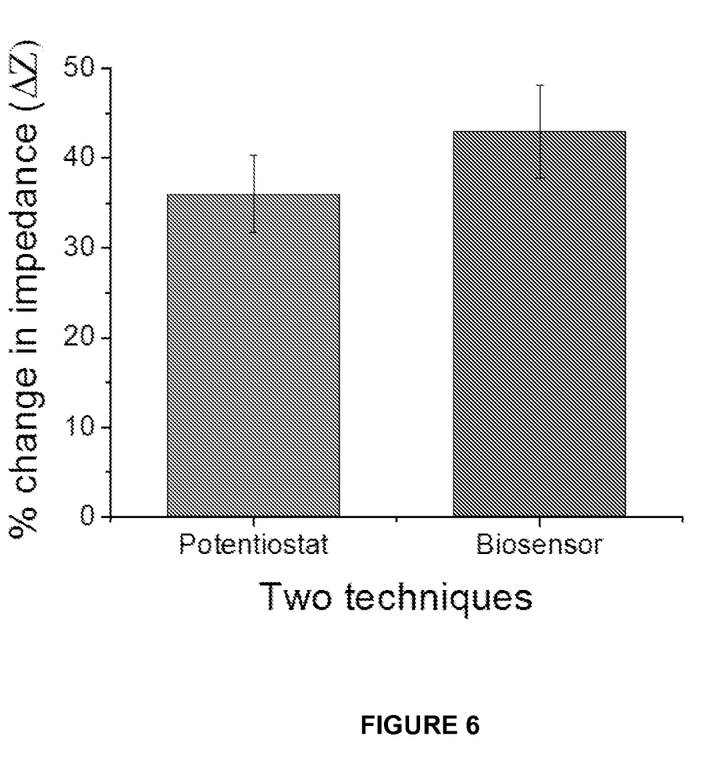
FIG. 6 is a bar graph showing the percentage change in impedance at 100K Hz from common corrosion testing and a MIEB, to verify the effectiveness using the MIEB as a sensor

The electrochemical results are presented in FIG. 4-5. The potentiodynamic curves for Used BCS (with metal ions) and Control BCS (base line data) exhibit considerable differences. There is an increase in the corrosion behavior of CoCrMo in Used BCS, is indicated by high $I_{corr}$ values and low $E_{corr}$ values compared to Control BCS. Interestingly, for the Used BCS, the polarization data shows an absence of typical transpassive behavior (FIG. 4). The impedance data is used to model equivalent circuit and the total impedance is estimated as shown in the FIG. 5. For Used BCS, lower impedance (Z) is observed compared to control which describes an increase in the corrosion kinetics of the CoCrMo sample in Used BCS. The percent change in the impedance (%$\Delta Z$) of the CoCrMo sample with Used BCS is approximately 36.03% (FIG. 6).

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A method for determining metal ion levels due to corrosion and wear (tribocorrosion) processes in a metallic implant present in a patient, comprising:
    adding a sample taken from the patient to an electrochemical cell, the sample comprising a fluid sample removed from the patient;
    measuring impedance at an electrode of the electrochemical cell to obtain a sample impedance value, wherein the sample impedance value is a measure of a presence of metal ions from the metallic implant in the fluid sample and is indicative of the metal ion levels released to a patient body due to corrosion process of the metallic implant;

comparing the measured impedance with a plurality of reference impedance values to obtain a comparison result, the plurality of reference impedance values obtained from a plurality of representative fluid samples with a plurality of cycles in a simulating tribocorrosion test;

determining whether a loss of metal ions from the metallic implant occurs based on the comparison result; and in response to determining that the loss of metal ions from the metallic implant occurs, determining a presence of implant corrosion.

2. The method of claim 1, wherein the fluid sample is selected from the group selected of a blood sample, a urine sample and a synovial fluid sample.

3. The method of claim 1, wherein the metallic implant comprises a metal component.

4. The method of claim 1, wherein the metallic implant is selected from the group consisting of a dental implant, a spinal implant, a hip joint, a knee joint, an ankle joint and a shoulder joint.

5. The method of claim 4, wherein the metallic implant is a hip joint.

6. The method of claim 1, where a metal in the metallic implant is selected from the group consisting of cobalt, chromium, molybdenum, titanium, vanadium, aluminum and a combination thereof.

7. The method of claim 1, wherein the electrochemical cell comprises
   a base platform;
   a reference electrode, a counter electrode and a working electrode on a surface of the base platform; and
   a housing unit positioned over the reference electrode, the counter electrode and the working electrode and forming a sample chamber in fluid contact with the reference electrode, the counter electrode, and the working electrode,
   wherein the housing unit comprises a sample entry port allowing addition of a liquid sample to the sample chamber.

8. The method of claim 1, wherein the impedance is measured using a potentiostat.

9. The method of claim 1 further comprising:
   adding one of the plurality of representative samples to the electrochemical cell; and
   measuring impedance at the electrode of the electrochemical cell to obtain one of the plurality of reference impedance values.

10. The method of claim 1, wherein the sample is collected from the patient between 2 and 36 months post-implantation of the metallic implant.

11. The method of claim 1, wherein the electrochemical cell comprises at least two electrodes in fluid-contact with a sample chamber.

12. The method of claim 11, wherein the electrochemical cell comprises three electrodes in fluid-contact with the sample chamber.

13. The method of claim 11, where the electrodes are gold electrodes.

* * * * *